United States Patent
Jackson et al.

(10) Patent No.: US 9,833,264 B2
(45) Date of Patent: *Dec. 5, 2017

(54) BI-RADIAL POP-ON CERVICAL BONE ANCHOR

(71) Applicant: Roger P. Jackson, Prairie Village, KS (US)

(72) Inventors: Roger P. Jackson, Prairie Village, KS (US); James L. Surber, Kansas City, KS (US)

(73) Assignee: Roger P. Jackson, Prairie Village, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 15/258,676

(22) Filed: Sep. 7, 2016

(65) Prior Publication Data

US 2017/0119438 A1 May 4, 2017

Related U.S. Application Data

(63) Continuation of application No. 14/591,651, filed on Jan. 7, 2015, now Pat. No. 9,451,993.

(60) Provisional application No. 61/925,420, filed on Jan. 9, 2014.

(51) Int. Cl.
*A61B 17/70* (2006.01)
*A61B 17/86* (2006.01)

(52) U.S. Cl.
CPC ........ *A61B 17/7037* (2013.01); *A61B 17/862* (2013.01)

(58) Field of Classification Search
CPC ............ A61B 17/7046; A61B 17/7038; A61B 17/7035; A61B 17/7037
See application file for complete search history.

(56) References Cited

U.S. PATENT DOCUMENTS

| | | |
|---|---|---|
| 5,672,176 A | 9/1997 | Biedermann et al. |
| 5,989,254 A | 11/1999 | Katz |
| 2002/0091386 A1* | 7/2002 | Martin ............... A61B 17/7037 606/278 |
| 2003/0149431 A1 | 8/2003 | Varieur et al. |
| 2004/0143265 A1 | 7/2004 | Landry |
| 2004/0147929 A1 | 7/2004 | Biedermann et al. |
| 2004/0186474 A1 | 9/2004 | Matthis et al. |
| 2006/0235392 A1* | 10/2006 | Hammer ............ A61B 17/7034 606/264 |
| 2008/0045963 A1 | 2/2008 | Abdou |

* cited by examiner

*Primary Examiner* — Julianna N Harvey
(74) *Attorney, Agent, or Firm* — Polsinelli PC (57) ABSTRACT

A cervical polyaxial bone anchor includes a longitudinal connecting member receiver structure and a cooperating shank. The shank has a body and an integral head with first and second spherical surfaces of different radii and a plurality of spaced curvate apertures for receiving portions of the longitudinal connecting member to result in a greater angle of inclination of the shank with respect to the receiver. The receiver has an upper channel and a lower cavity that further includes an expansion area and an operational seat for a split retainer ring that captures and fixes the shank head within the receiver.

15 Claims, 9 Drawing Sheets

BI-RADIAL POP-ON CERVICAL BONE ANCHOR

RELATED APPLICATIONS

This continuation application claims priority under 35 U.S.C. §120 from co-pending U.S. Nonprovisional application Ser. No. 14/591,651 entitled "BI-RADIAL POP-ON CERVICAL BONE ANCHOR," filed Jan. 7, 2015, which claims priority under 35 U.S.C. §119 from U.S. Provisional Application No. 61/925,420 entitled "BI-RADIAL POP-ON CERVICAL BONE ANCHOR," filed Jan. 9, 2014 the entire contents of which are fully incorporated by reference herein for all purposes.

BACKGROUND OF THE INVENTION

The present invention is directed to polyaxial bone anchors for use in bone surgery, particularly spinal surgery and particularly to such bone anchors with retainers for capturing and retaining a bone screw shank head in the receiver member assembly and later fixing the bone screw shank with respect to the receiver assembly.

Bone screws are utilized in many types of spinal surgery in order to secure various implants to vertebrae along the spinal column for the purpose of stabilizing and/or adjusting spinal alignment. When vertebrae of the cervical spine are involved, the connecting structure or structures commonly include a plate and cooperating relatively smaller screws. When the connector is in the form of a rod, both closed-ended and open-ended bone screws are known with open-ended screws being particularly well suited for connections to rods and connector arms because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or rod receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable and make the procedure more difficult, but desirable in other situations.

SUMMARY OF THE INVENTION

An embodiment of the present invention is a polyaxial spinal bone screw assembly for receiving and fixing placement of a longitudinal connecting member such as a rod. The assembly includes a bone screw shank having a body for insertion into bone integral with an upper portion or head. The shank head includes a top convex partially spherical first surface having a first radius and a lower convex partially spherically shaped surface having a second radius. A third annular surface extends outwardly from the first surface and terminates at the second surface at a spheric perimeter or edge. At least one and up to a plurality of spaced concave surface features are formed through the edge and thus into the annular and lower spherical surfaces. A rod or other longitudinal connector receiver structure has a pair of arms forming a channel as well as base that defines a cavity. The cavity is sized to allow for pivotal movement of the shank first and second surfaces there within. A lower opening communicates with the cavity and an exterior of the receiver opposite the pair of arms. The cavity communicates with the channel. The receiver cavity is further defined by a lower seat and an expansion area located above the lower seat. The bone screw head is uploaded and received in the cavity through the lower opening. The assembly further includes an open and resilient ring-like retainer receivable in the cavity and outwardly biased against the receiver in fixed relation thereto at the receiver seat when the shank head is captured in the receiver and fixed against the retainer by a downward force placed directly on the head by a rod or other longitudinal connecting member so as to fix or lock an angular position of the receiver relative to the shank. The retainer is expandable about the shank head at the receiver cavity expansion area during uploading of the shank head through the receiver lower opening. Prior to locking, the shank head is in sliding, pivotable relation with the retainer and the retainer is rotatable with respect to the receiver. Also, while still in an unlocked position a portion of the rod may be received in an area defined by one of the shank concave surface features to provide an increased angle of articulation between the shank and the receiver. Thereafter, another portion of the rod may then be fixed into locking engagement with the shank first convex surface.

Objects of the invention include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Figure 1:
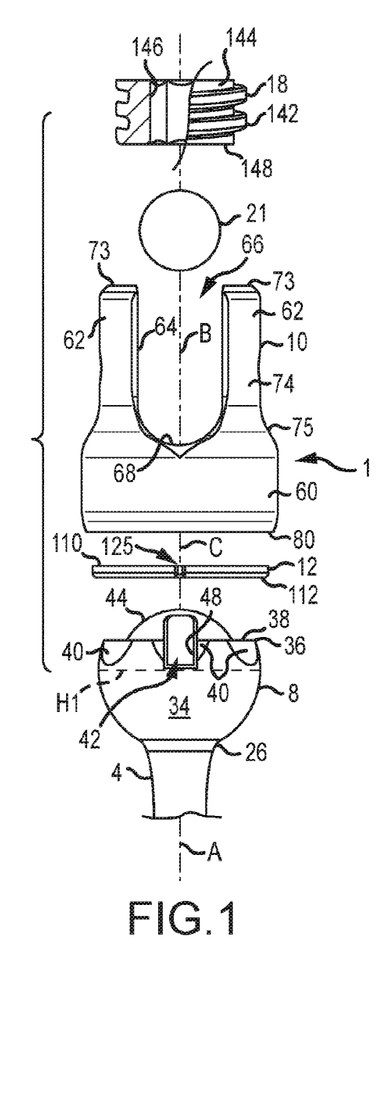
FIG. 1 is an exploded and partial front elevational view of a polyaxial bone screw assembly according to an embodiment of the present invention including a shank, an open retainer and a receiver and further showing a cooperating rod and closure top shown with portions broken away to show the detail thereof.

With reference to FIG. 1, the reference number 1 generally represents a polyaxial bone screw apparatus or assembly according to an embodiment of the present invention that includes a shank 4 that further includes a body 6 integral with an upwardly extending upper portion or head-like capture structure 8; a receiver 10; and an open ring retainer structure 12. The receiver 10 and retainer 12 are initially assembled by the vendor and may be further assembled with the shank 4 either by the vendor or by a user prior to or after implantation of the shank body 6 into a vertebra 17, as will be described in greater detail below. Thus, when desired, the shank 4 may be implanted into a vertebra first, followed by assembly with the other components. Even though such a procedure might not at first blush appear desirable on the smaller, more fragile cervical vertebrae, due to the small size of the assembly 1 and that only between about forty and about fifty inch pounds of torque is required for attaching a closure structure 18 to the receiver 10 to capture and fix a longitudinal connecting member, such as a rod 21 to the assembly 1, the initial posting or implantation of the shank 4 followed by a push- or snap-on assembly with the receiver 10 is acceptable and may be a desired procedure in some circumstances. FIG. 1 further shows such closure structure 18 for capturing the longitudinal connecting member, for example, shown as a 3.5 millimeter diameter rod 21 which in turn engages the shank head 8 that in turn presses into fixed frictional contact with the retainer 12, so as to capture, and fix the longitudinal connecting member 21 within the receiver 10 and thus fix the member 21 relative to the vertebra 17.

The illustrated rod 21 is hard, stiff, non-elastic and cylindrical; however, it is foreseen that in other embodiments, the rod 21 may be elastic, deformable and/or of a different cross-sectional geometry. Although a 3.5 mm diameter rod is shown, the rod for use with the cervical assembly 1 could be smaller or bigger, with diameter measurements of 3.0 mm, 3.75 mm and 4.0 mm also being common (and with the receiver 10 being sized accordingly to cooperate with such diameter size). In some embodiments, the bone screw assembly 1 may also cooperate with soft connecting systems, such as spinal connectors having rigid sleeves for placement within bone screw receivers in lieu of a rod, such sleeves including through bores for receiving a tensioned cord, for example.

As will be described in greater detail below the receiver 10 and the head 8 of the shank 4 cooperate in such a manner that the receiver 10 and the shank 4 can be secured at a plurality of different angles, articulations and rotational alignments relative to one another and within a selected range of angles both from side to side and from front to rear, to enable flexible or articulated engagement of the receiver 10 with the shank 4 until both are locked or fixed relative to each other near the end of an implantation procedure. The drawings at FIGS. 19-21 also illustrate a driver, generally 24 for use with the assembly 1 as will be described in greater detail below.

The shank 4, best illustrated in FIGS. 1-4, is elongate, the shank body 6 being only partially shown in the drawing figures. The body 6 is elongate and further includes one or more helically wound threads for bone engagement that are known in the art of pedicle screws, in particular smaller screws sized and shaped for use on the cervical spine. An example of a larger pedicle screw shank for use with some embodiments of the invention is illustrated, for example, in U.S. Pat. No. 6,726,689, which is also incorporated herein by reference to provide examples of flange form guide and advancement structures for use with receivers 10 and closures 18 of embodiments of the invention. During use, the body 6 utilizing the thread or threads (not shown) for gripping and advancement is implanted into the vertebra 17 (e.g., see FIG. 20) leading with a tip of the shank 6 and driven down into the vertebra with an installation or driving tool, such as the tool 24, so as to be implanted in the vertebra to a location at or near a neck thereof, as more fully described in the paragraphs below. The shank 4 has an elongate axis of rotation generally identified by the reference letter A.

A neck 26 extends axially upward from the shank body 6. The neck 26 may be of the same or of a slightly reduced radius as compared to an adjacent upper end or top of the body 6 where the thread or threads terminate. Extending axially upwardly and radially outwardly from the neck 26 is the shank upper portion or head 8 that provides a connective or capture apparatus disposed at a distance from the threaded portion of the shank 6 and thus at a distance from the vertebra 17 when the body 6 is implanted in such vertebra.

Figures 4, 5, 6, 7:
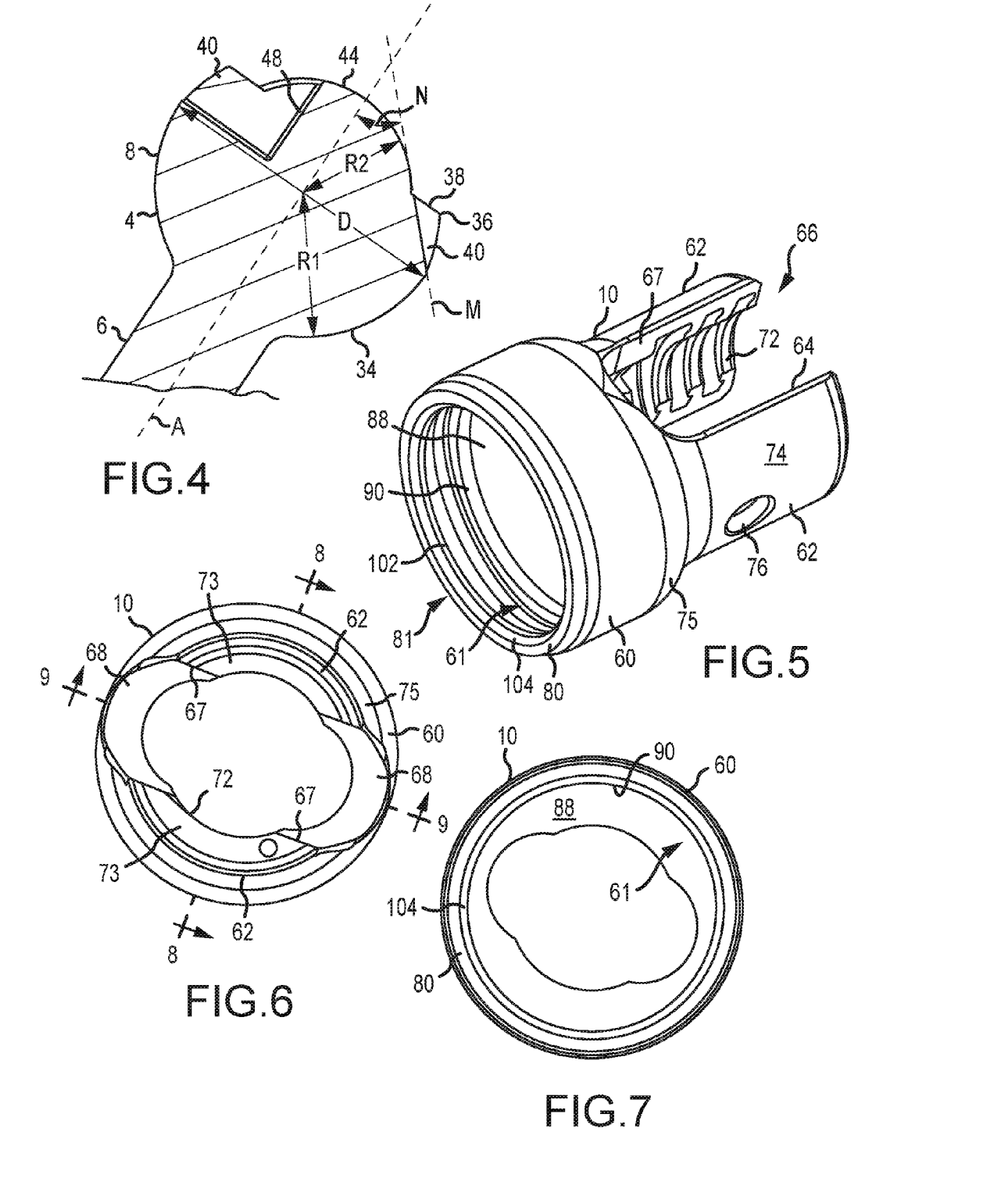
FIG. 4 is a cross-sectional view taken along the line 4-4 of FIG. 3.
FIG. 5 is an enlarged perspective view of the receiver of FIG. 1.
FIG. 6 is a top plan view of the receiver of FIG. 5.
FIG. 7 is a bottom plan view of the receiver of FIG. 5.
Figure 8:
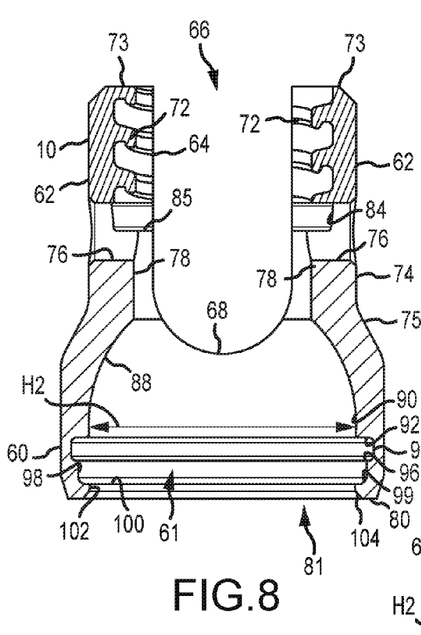
FIG. 8 is a cross-sectional view taken along the line 8-8 of FIG. 6.
Figure 9:
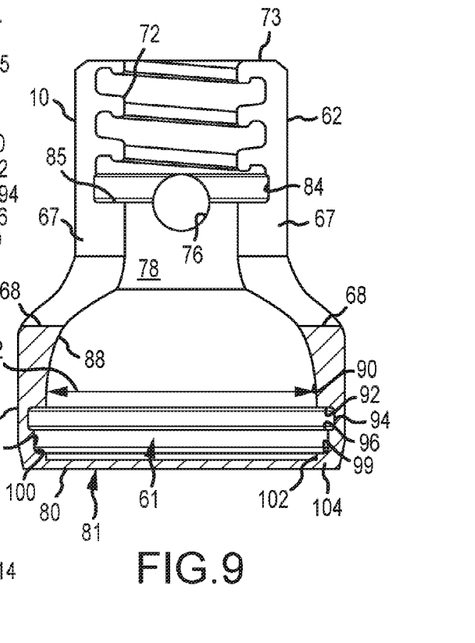
FIG. 9 is a cross-sectional view taken along the line 9-9 of FIG. 6.
Figure 10:
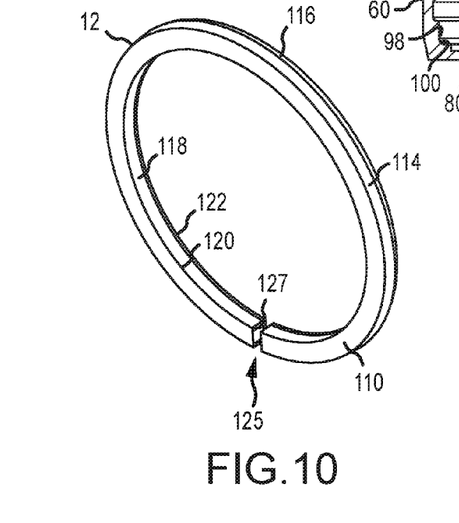
FIG. 10 is an enlarged perspective view of the open retainer of FIG. 1.
Figure 11:
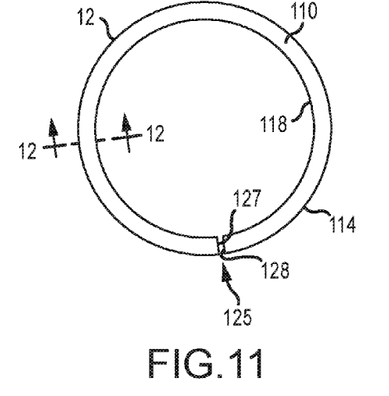
FIG. 11 is a reduced top plan view of the retainer of FIG. 10.
Figure 12:
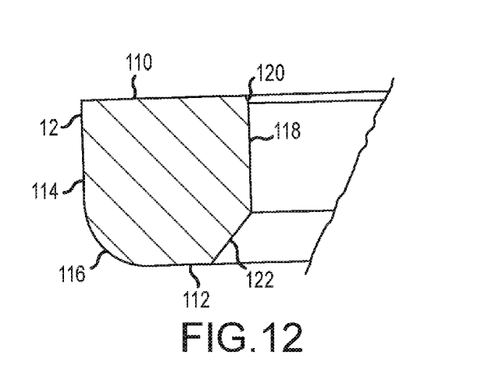
FIG. 12 is an enlarged and partial cross-sectional view taken along the line 12-12 of FIG. 11.

The shank upper portion or head 8 is configured for engagement between the portion 8 and the retainer 12 (ultimately an operative fixed, frictional engagement) and a pivotable connection between the shank 4 and the receiver 10 prior to fixing of the shank 4 in a desired position with respect to the receiver 10. The shank head or upper portion 8 has a first outer, convex and substantially spherical surface 34 that extends outwardly and upwardly from the neck 26. A dotted line H1 in FIG. 1 indicates a hemisphere of the lower spherical surface 34 that has a maximum or major diameter D at such hemisphere H1 as shown in FIG. 4. A radius R1 shown in FIG. 4 is the radius of the surface 34 at the major diameter D so D=2R1. The spherical surface 34 radius R1 is configured for frictional sliding and then ultimate fixed cooperation with the retainer 12 as will be discussed more fully in the paragraphs below. The shank spherical surface 34 is locked into place at the retainer 12 and not by inner surfaces defining the receiver 10 cavity, the shank head 8 being held in spaced relation with the receiver 10 by the retainer 12. The spherical surface 34 shown in the present embodiment is substantially smooth, but in some embodiments may include a roughening or other surface treatment to enhance frictional engagement with the retainer 12. The surface 34 terminates at a circular spheric edge 36 that extends around a perimeter of the surface 34 and intersects with and also partially defines an outer perimeter of a discontinuous annular surface 38 located spaced from and above the hemisphere H1. The annular surface 38 and the adjacent spherical surface have formed thereon a plurality of uniformly formed and spaced curvate concave surfaces 40 as well as a multi-pronged drive receiving feature, generally 42, that will be described in greater detail below. The surface 38 is substantially planar and disposed perpendicular to the axis A. The surface 38 extends radially inwardly of the spherical surface 34 starting at the spheric edge 39 and terminates at a second convex and substantially spherical upper surface or dome 44. The dome 44 has a radius R2 that is smaller than the radius R1 of the spherical surface 34. Both the radii R1 and R1 are measured from the shank central axis A. The domed surface 44 radius is configured such that the rod 21 directly engages and is fixable against the surface 44 at any and all operative angular configurations of the shank 4 with respect to the receiver 10. The illustrated domed surface 44 is smooth. However, the surface 44 may include ridges, a roughening or other surface treatment to provide enhanced frictional contact between the rod 21 and the surface 44.

Figure 2:
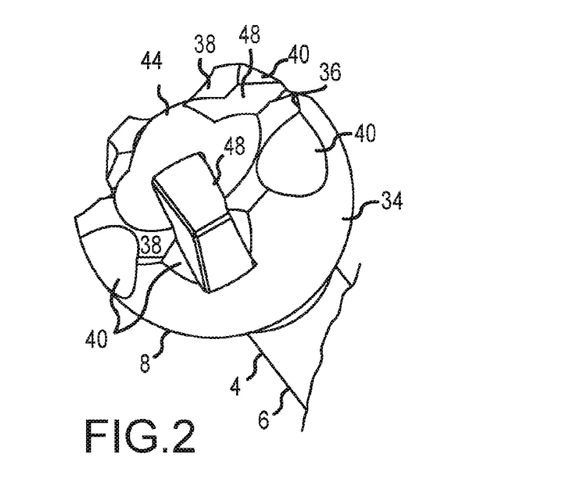
FIG. 2 is an enlarged and partial perspective view of the shank of FIG. 1.
Figure 3:
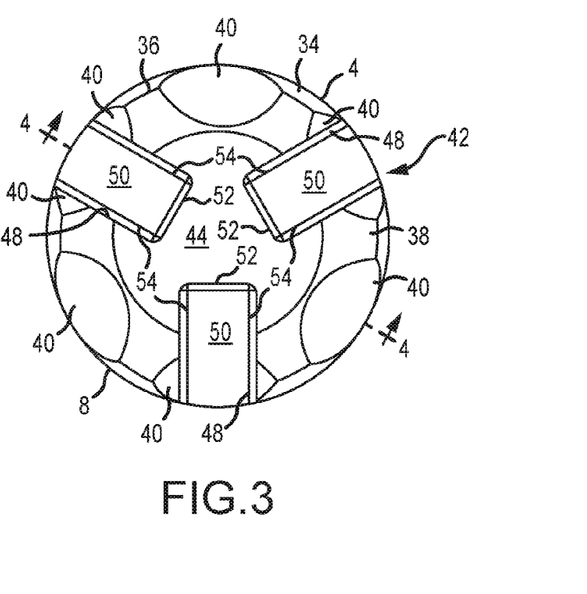
FIG. 3 is an enlarged top plan view of the shank of FIG. 2.

With further reference to FIGS. 2 to 4, there are six substantially evenly spaced apertures or cut-out surfaces 40 of identical or substantially similar size and shape that are formed into the shank head surfaces 34 and 38 and thus into the perimetric spheric edge 36. Thus, the loading edge 36 that is substantially circular and located above the hemisphere H1 is made discontinuous by the six arcuate surface formations 40. Three of the surface features 40 further include a drive slot 48 of the drive feature 42 as will be described in greater detail below. Each of the surfaces 40 is sized and shaped so as to provide a partially curved or partially cylindrical seat to receive a portion of the rod 21 as shown, for example in FIGS. 23-25 to allow for an increased or maximum angle of inclination of the shank 4 with respect to the receiver 10, which in the illustrated embodiment is approximately forty-four degrees. Thus, as shown in FIG. 4 each surface 40 is configured to receive the rod 21 along or near a line M that forms an angle N with respect to the shank axis A that in the illustrated embodiment is approximately forty-four degrees. It is foreseen that in other embodiments of the invention the angle N may be greater or smaller. However, for angles greater than forty-four degrees, the cylindrical or curved cut-out area provided by each surface portion 42 would also be wider which might eliminate or substantially reduce the size of the annular surface 38 and thus the loading edge 36 of the spherical surface 34 located between each of the curved cut-outs 40. Such a decrease of the loading edge 36 located between each surface feature 40 would not be desirable as the spheric loading edge 36 and the spherical loading surfaces 34 located adjacent and below the edge 36 are sized for securely retaining the head 8 within the ring 12 and thus prohibiting pull-out of the shank head 8 from the receiver 10 when the shank 4 is pivoted at higher angles such as the forty-four degree angle shown in FIG. 23, for example. It is noted that in other embodiments more or fewer formations 40 may be used. The illustrated combination of spaced concave surface formations 40, each with adjacent spherical surface portions 34 that terminate at the spheric edge 36, advantageously result in the bi-radial shank 4 that may be pivoted to up to about 44 degrees with respect to a cooperating rod 21 at a plurality of locations on the shank head 8 and thus at a plurality of positions with respect to the receiver 10 while keeping such shank head 8 securely within the receiver 10. It is noted that the term bi-radial in this application may apply to two different aspects of the shank head 8. In a first aspect, the shank head 8 has a first spherical surface 34 with a first radius R1 and a second spherical surface 44 or dome that engages the rod that has a second, smaller radius R1. In a second aspect, the illustrated shank 4 may be described as having a bi-radial symmetry because the concave cuts or surface formations 40 are located opposite one another on either side of the axis A and one surface portion 34 having the upper support edge 36 is located adjacent to and between each formation 40.

Figures 18, 19:
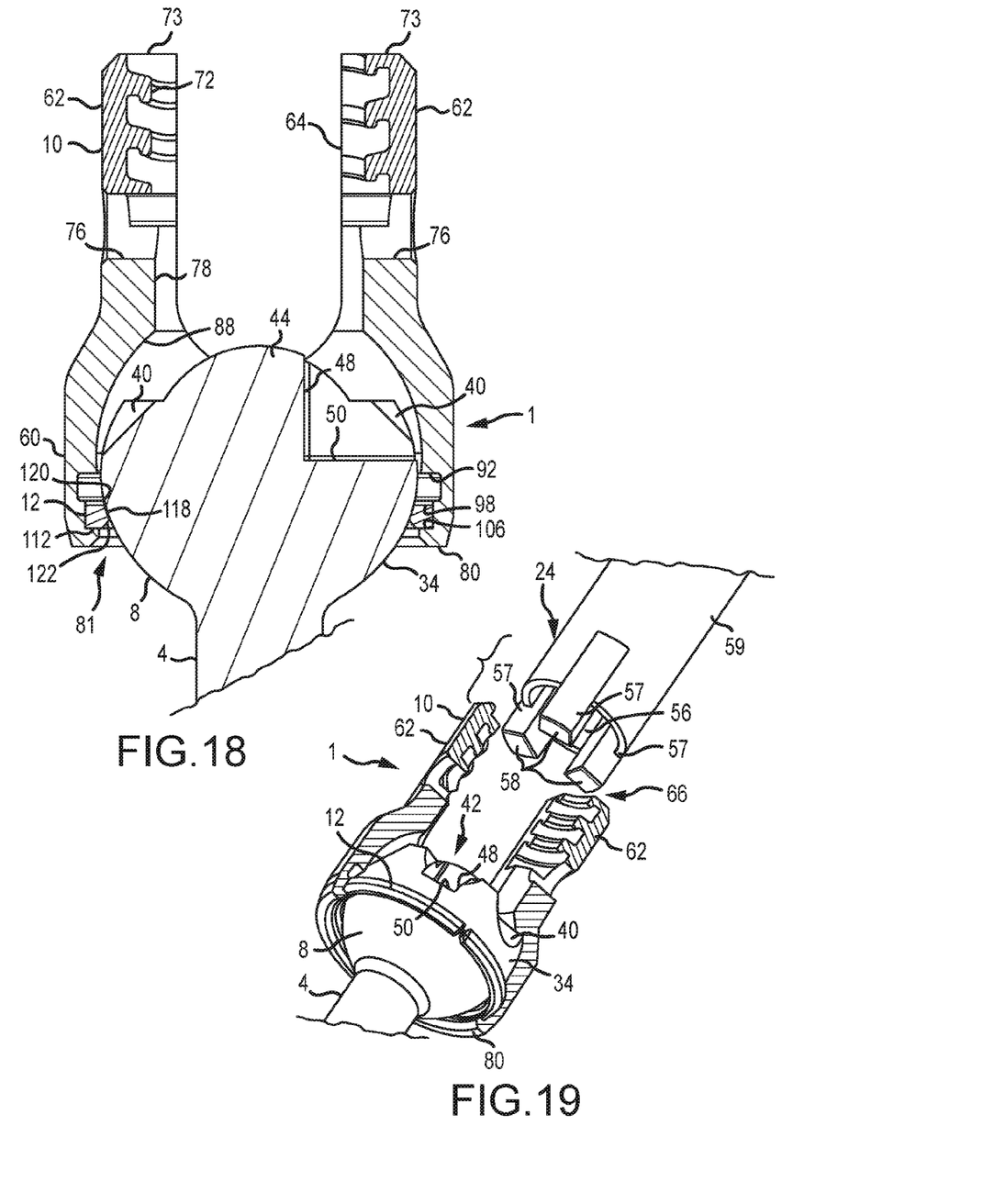
FIG. 18 is a partial front elevational view with portions broken away, similar to FIG. 17, showing the shank head lowered to a seated position on the retainer.
FIG. 19 is a reduced and partial perspective view with portions broken away of the assembly as shown in FIG. 18 and further showing a shank driver tool, also in partial perspective view.
Figures 20, 21, 22:
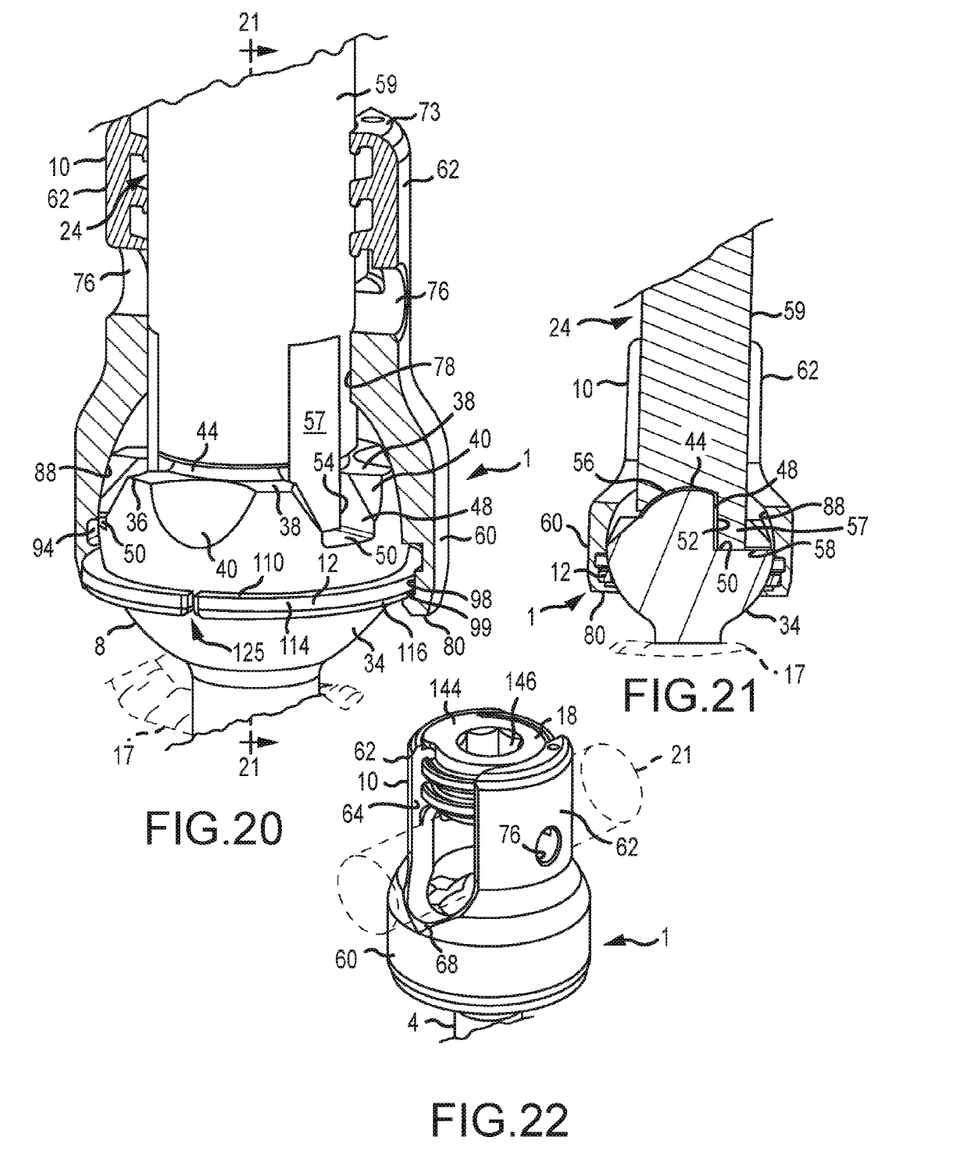
FIG. 20 is an enlarged and partial perspective view with portions broken away of the assembly of FIG. 19, showing the driver engaged with the shank to drive the shank into a vertebra, shown in a partial and partially schematic view.
FIG. 21 is a reduced and partial cross-sectional view taken along the line 21-21 of FIG. 20.
FIG. 22 is a reduced and partial perspective view of the assembly of FIG. 20 further shown assembled with the rod and closure of FIG. 1, also in perspective view, the rod in phantom to show details of the assembly.
Figures 25, 26:
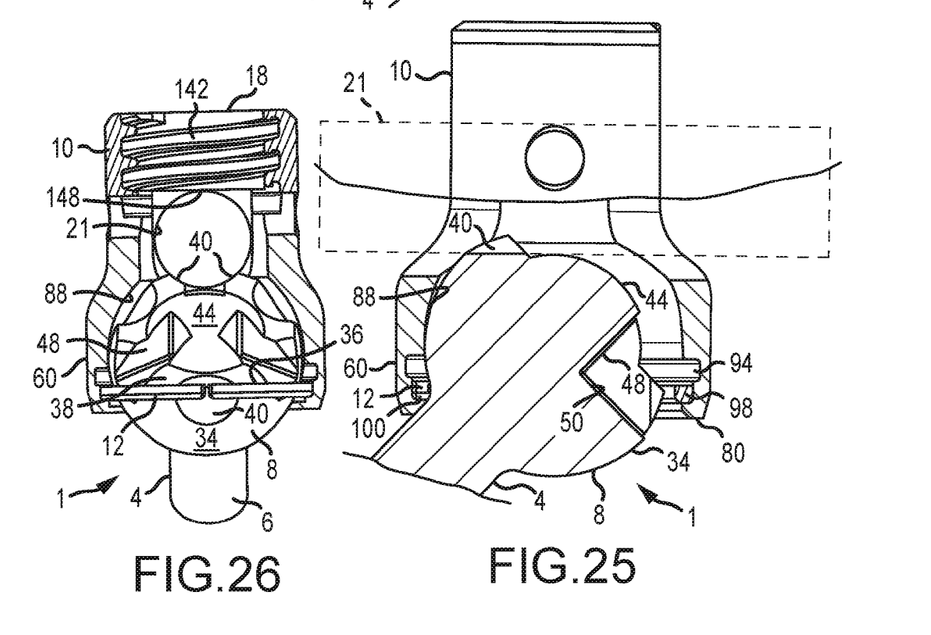
FIG. 25 is an enlarged and partial side elevational view with portions broken away of the assembly of FIG. 22, but with the shank pivoted to a forty-four degree angle with respect to the receiver in the sagittal plane with the shank pivoted in a cephalic direction, the rod in phantom to show details of the assembly.
FIG. 26 is a reduced and partial rear elevational view of the assembly of FIG. 25 with portions of the receiver broken away to show details of the assembly.

As best shown in FIG. 3, the internal drive feature 42 that includes the three drive slots or grooves 48 is formed in an upper portion of the head 8, specifically in the domed surface 44, the annular surface 38 and three of the concave features 40. Each drive slot 48 includes a counter sunk substantially planar base 50 an inner planar wall 52 and planar opposed side walls 54. Each slot 48 is open at the head spherical surface 34 and extends radially inwardly toward the axis A. Each slot 48 extends into the convex domed surface 44, but the slots 48 do not intersect or otherwise communicate with one another at the surface 44, leaving a substantial portion of the surface 44 located on and near the axis A intact for providing adequate surface area for frictional engagement between the spherical surface 44 and the rod 21 or other longitudinal connecting member. With reference to FIGS. 19-21, the driver 24 is equipped with an inner concave spherical surface 56 and three outer, evenly spaced prongs 57 sized and shaped for insertion over the domed surface 44, with the three prongs brining received by the three radially extending slots 48 of the feature 42. Each prong 57 has a substantially planar end surface 58 sized and shaped for frictional engagement with one of the drive slot base surfaces 50, the prongs 57 being evenly spaced and illustrated as being fixed to (or may be integral with) a substantially cylindrical elongate shaft 59. The shaft 59 may be part of a larger holding and driving tool system known in the art. The three slots 48 of the drive feature 42 are substantially uniform and are sized and spaced such that the slots 48 run centrally through every other curvate surface feature 40 with a portion of the surface feature 40 being cut by the slot 48 remaining on either side of each slot 48. Thus the rod 21 or other longitudinal connecting member may only engage the surface feature 40 on either side of the slot 48 and cannot enter more deeply into a space defined by the drive slot 48 (as shown in FIG. 26, for example). It is foreseen that in other embodiments, the three-drive slot drive feature 42 on the shank head 8 may take other tool-engaging forms and may include, for example, fewer or more apertures or slots of various shapes, such as a pair of spaced apart apertures, for example. The illustrated seat or base surface 50 of each drive slot 48 of the drive feature 42 is disposed substantially perpendicular to the axis A with the drive feature 42 being coaxial with the axis A. The illustrated drive seats 50 further include beveled or stepped surfaces that may further enhance gripping with the driving tool 24 at the prongs 57. As will be described in greater detail below, in operation, the driving tool prongs 57 are received in the internal drive slots 48, being seated at the base surfaces 50 and engaging the side walls 54 for rotating and driving the shank body 6 into the vertebra 17, either before the shank 4 is attached to the receiver 10 or after the shank 4 is attached to the receiver 10, with the shank body 6 being driven into the vertebra 17 with the driving tool extending into the receiver 10 as shown in FIGS. 20 and 21, for example.

The shank 4 shown in the drawings is solid, but in some embodiments may be cannulated, having a small central bore extending an entire length of the shank 4 along the axis A. Such a bore is typically defined by an inner cylindrical wall of the shank 4 having a circular opening at the shank driving tip and an upper opening at the domed top 44. Such a bore is typically coaxial with the threaded body 6 and the upper portion 8. Such a bore provides a passage through the shank 4 interior for a length of wire (not shown) inserted into the vertebra 17 prior to the insertion of the shank body 6, the wire providing a guide for insertion of the shank body 6 into the vertebra 17.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2)$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 5-9, the receiver 10 has a generally U-shaped appearance with various discontinuous and continuous curved inner and outer profiles. The receiver 10 has a central axis of rotation B that is shown in FIG. 1 as being aligned with and the same as the axis of rotation A of the shank 4, such orientation being desirable during assembly of the receiver 10, retainer 12 with the shank 4. After the receiver 10 is pivotally attached to the shank 4, the axis B is typically disposed at an angle with respect to the axis A, as shown, for example, in FIGS. 23-28.

The receiver 10 includes a base or lower body portion 60 that is illustrated as having a cylindrical outer surface, that in some embodiments may include other outer surface geometries, including curved, frusto-conical and partially planar. The base 60 defines a bore or inner cavity, generally 61, the base 60 being integral with a pair of opposed upstanding arms 62 forming a cradle and defining a channel 64 between the arms 62 with an upper opening, generally 66. The channel 64 is further defined by partially planar interior arm surfaces 67 that transition to a U-shaped lower saddle or seat 68, the channel 64 having a width for operably snugly receiving the rod 21 or portion of another longitudinal connector between the arms 62; the channel 64 communicating with the base cavity 61.

Each of the arm interior surfaces 67 have formed or machined therein various inner cylindrical profiles, an upper one of which is a partial helically wound guide and advancement structure 72 located adjacent a top surface or rim 73 of each of the arms 62. In the illustrated embodiment, the guide and advancement structure 72 is a partial helically wound interlocking flangeform configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-thread-like helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms could have break-off extensions in some embodiments.

Outer surfaces 74 of each arm 62 are substantially cylindrical and further include frusto-conical or curved transition surfaces 75 that extend radially outwardly to transition to the substantially cylindrical base 60. A pair of opposed substantially cylindrical through bores 76 are located centrally in the arms 72, each bore formed on one of the outer surfaces 74 and extending through the arm inner surface at a cylindrical portion 78 thereof located beneath the guide and advancement structure 72. The opposed bores 76 may be used with tools for holding the receiver 10 during assembly with the other components (12 and 4) of the bone anchor assembly 1 and during implantation and manipulation of the assembly 1 during surgery, for example. It is foreseen that other tool receiving grooves, depressions or apertures may be configured in a variety of shapes and sizes and be disposed at other locations on the receiver arms 62 and receiver base 60. Below the u-shaped seat 68, the substantially cylindrical base 60 eventually tapers inwardly slightly and then terminates at a substantially planar bottom surface 80 that partially defines an opening, generally 81 into the receiver cavity 61.

Returning to the interior surfaces 67 of the receiver arms 62, located below each guide and advancement structure 72 is a discontinuous cylindrical surface 84 partially defining a run-out feature for the guide and advancement structure 72. The cylindrical surface 84 has a diameter equal to or slightly greater than a greater diameter of the guide and advancement structure 72. Moving downwardly in a direction toward the base 60, adjacent the cylindrical surface 94 of each arm is a run-out seat or surface 85 that extends inwardly toward the axis B and is substantially perpendicular to the axis B. In other embodiments, the surface 85 may gently slope downwardly toward the axis B. Adjacent to and located below the surface 85 are planar inner arm surface portions as well as the centrally located cylindrical surface portion 78 through which the bore 76 extends. Portions of each bore 76 also extend through the cylindrical surface 84 and the run-out seat 85. The surface 78 terminates at a concave substantially spherical surface 88 that extends downwardly along each inner arm 67 and also between and below the curved surfaces defining the u-shaped channel seat 68, the surface 88 thus defining an upper portion of the base cavity 61 where the cavity 61 communicates with the u-shaped channel 64. The partially spherical or radiused surface 88 terminates at a largest diameter or hemisphere H2 thereof (shown in phantom) with H2 being slightly larger and thus slightly greater in diameter than the diameter D of the shank head surface 34 having the hemisphere H1. At the hemisphere H2, the surface 88 transitions into a cylindrical surface 90. The surface 90 terminates at an overhang or ceiling surface 92. The surface 92 is annular and perpendicular to the axis B. The surface 92 extends radially outwardly to a cylindrical surface 94 that terminates at a lower annular seat or ledge 96. The surfaces 92, 94 and 96 define an expansion chamber for the retainer 12 as will be described in greater detail below. The surface 92 is perpendicular to the cylindrical surface 94. The surface 96 curves or slopes slightly downwardly and inwardly toward and to another cylindrical surface and 98 that transitions to an annular surface or operation seat 100 for the retainer 12. The illustrated surfaces 98 and 100 are connected by one or more curved or sloping surfaces 99, the surfaces 98, 99 and 100 operationally capturing and seating the retainer 12 against the receiver 10 as will be described in greater detail below; the retainer 12 in turn capturing the shank 8 within the receiver cavity 61. The surface 100 terminates at another cylindrical surface 102. The cylindrical surface 94 has a diameter greater than a diameter of the cylindrical surface 98 that in turn has a diameter greater than a diameter of the cylindrical surface 102. The diameter of the surface 102 is substantially the same or slightly greater than the diameter measured at the hemisphere H2 of the radiused surface 88 that is also the diameter of the cylindrical surface 90. Thus, the surface 102 is sized to receive the shank head 8 at the greatest diameter D thereof. The cylindrical surface 102 terminates at an outwardly flaring frusto-conical surface 104 that terminates at the base surface 80, the surfaces 102, 104 and 80 forming the lower opening 81 of the receiver cavity 61.

Figure 13:
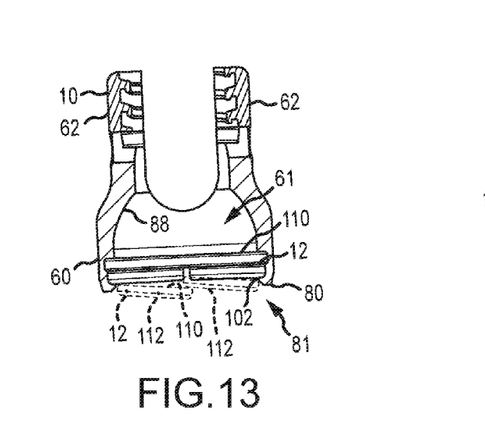
FIG. 13 is a reduced front elevational view of the receiver and retainer of FIG. 1 shown in a stage of assembly, the retainer shown in phantom in an earlier stage of assembly and the receiver shown with portions broken away to show the detail thereof.

With particular reference to FIGS. 1 and 10-12, the rotatable split or open, ring-like resilient retainer 12 includes the following features: a top discontinuous and substantially planar surface 110; an opposed discontinuous substantially planar bottom surface 112 that runs parallel to the top surface 110; a discontinuous outer cylindrical surface 114 perpendicular to both the top 110 and bottom 112 surfaces; a curved convex transition surface 116 extending between the outer cylindrical surface 114 and the bottom surface 112; a discontinuous inner cylindrical surface 118 spaced from and concentric with the outer cylindrical surface 114; an upper inner frusto-conical surface or bevel 120 extending from the top surface 110 and running inwardly and downwardly toward a central axis C of the retainer 12 and terminating at the inner cylindrical surface 118; and a lower inner frusto-conical surface 122 beginning at a termination of the inner cylindrical surface 118 and extending downwardly and outwardly away from the axis C and terminating at the bottom surface 112. When assembled with the receiver 10, the retainer 12 central axis C is the same as the central axis of rotation B of the receiver 10. When in a neutral state and in an expanded state, the retainer 12 top and bottom surfaces are substantially uniformly planar and parallel. However, as shown in FIG. 13, when the resilient retainer 12 is compressed or contracted during assembly with the receiver 10, portions of the retainer may overlap as will be described in greater detail below. This is possible due to the resiliency and small size of the retainer 12 and a small slit or gap, generally 125 located between opposed end surfaces 127 and 128 of the retainer 12. The surfaces 127 and 128 are slightly spaced from one another, both the surfaces 127 and 128 being substantially perpendicular to the top surface 110. In other embodiments, the surfaces 127 and 128 may not be parallel to one another or both surfaces may be at a similar oblique angle with respect to the top surface 110. It is foreseen that in some embodiments of the invention, the retainer 12 may have more or fewer planar and cylindrical surfaces. In other embodiments, the retainer 12 may be circular in cross-section, e.g., in the form of a split ring or wire. In the illustrated embodiment, the retainer 12 surface geometry results in the inner upper frusto-conical surface 120, or at least a portion or edge thereof being in operative, fixed frictional engagement with the spherical surface 34 of the shank head 8 when the retainer outer cylindrical surface 114 is pressed against the receiver cylindrical surface 98 and the retainer outer curved transition surface 116 is seated against the receiver transition surface 99 with the retainer base surface 112 being seated on the receiver annular surface 100 due to downward pressure of the shank head 8 against the retainer 12 (see, e.g., FIGS. 23-29).

With reference to FIGS. 1 and 22-29, for example, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface of uniform diameter. The illustrated rod 21 is sized for use on the cervical spine and thus has a diameter of 3.5 mm and may have a diameter as small as about 3.0 mm and as large as about 4.0 mm. The rod 21 may be made from a variety of metals, including hard and soft metal alloys and hard and soft or deformable and less compressible plastics, including, but not limited to rods made of elastomeric, polyetheretherketone (PEEK) and other types of materials.

In other embodiments, it is foreseen that longitudinal connecting members for use with the assembly 1 may take a variety of shapes, including but not limited to rods or bars of oval, rectangular or other curved or polygonal cross-section. Some other embodiments may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the receiver 10. The longitudinal connecting member may be integral or otherwise fixed to a bendable or damping component that is sized and shaped to be located between adjacent pairs of bone screw assemblies, for example. A damping component or bumper may be attached to the longitudinal connecting member at one or both sides of the bone screw assembly. A rod or bar (or rod or bar component) of a longitudinal connecting member may be made of a variety of materials ranging from soft deformable plastics to hard metals, depending upon the desired application. Thus, bars and rods may be made of materials including, but not limited to metal and metal alloys including but not limited to stainless steel, titanium, titanium alloys and cobalt chrome alloys; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 22-29, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes an outer helically wound guide and advancement structure 142 in the form of a flange that operably joins with the guide and advancement structure 72 disposed on the arms 62 of the receiver 10. The flange form utilized in accordance with embodiments of the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to control an amount of splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the small size of the cervical screw and longitudinal connecting member. A single start flange form 142 is illustrated; however, it is foreseen the closure 18 may have two starts with cooperating flange form structure on the receiver arms 62. The illustrated closure structure 18 also includes a top surface 144 with an internal drive 146 in the form of an aperture that is illustrated as a hex-shaped internal drive, or may be, for example, a star-shaped or Torx drive, or other internal drives such as slotted, tri-wing, spanner, two or more apertures of various shapes, and the like. A driving tool (not shown) sized and shaped for engagement with the internal drive 146 is used for both rotatable engagement and, if needed, disengagement of the closure 18 from the receiver arms 62. It is also foreseen that in larger embodiments, the closure structure 18 may alternatively include a break-off head designed to allow such a head to break from a base of the closure at a preselected torque. Such a closure structure would also include a base having an internal drive to be used for closure removal. The drive extends all the way through the closure to a bottom surface 148 of the closure and may include a rim in some embodiments. The drive provides a cannulation through bore extending along a central axis thereof and through the top and bottom surfaces thereof. Such a through bore provides a passage through the closure 18 interior for a length of wire (not shown) inserted therein to provide a guide for insertion of the closure top into the receiver arms 62 in some embodiments an methods.

The components of the assembly 1, closure top 18 and the rod 21 may be made from a variety of materials including metals and non-metals, including, but not limited to titanium, titanium alloys, stainless steel, cobalt chrome alloys, polymers such as polyetheretherketone (PEEK) and carbon fiber polymers. For example, the assembly may include a retainer 12 preferably made from titanium, a titanium alloy or a cobalt chrome alloy and the cooperating receiver and shank may also be made from any of those materials. A particularly preferred retainer 12 is made from a cobalt chrome alloy. However, it is noted when the retainer 12 is made from cobalt chrome, a cooperating receiver 10 and shank 4 should not be made from stainless steel.

With reference to FIGS. 13-18, the receiver 10 and retainer 12 are preferably assembled at a factory setting that includes tooling for holding and alignment of the component pieces as well as compressing the retainer 12 prior to insertion into the receiver 10. In some circumstances, the shank 4 is also assembled with the receiver 10 and retainer 12 at the factory. In other instances, it may be more desirable for the surgical staff to pre-assemble a shank of a desired size and/or variety (e.g., surface treatment of roughening the upper portion 8 and/or hydroxyapatite on the shank 6), with the receiver and retainer. Allowing the surgeon to choose the appropriately sized or treated shank 4 advantageously reduces inventory requirements, thus reducing overall cost. Also, it may be desirable in some instances to implant the shank 4 into a vertebra first, followed by pressing the retainer (that is already captured in the receiver) over the shank. In some instances, this may not be desirable due to the small size of the assembly 1 and the fragile nature of the smaller cervical spine vertebrae for which the assembly 1 is designed.

In addition to being inventory friendly as described above, the assembly 1 components may be provided to the end user in a tracking friendly and sterilization friendly manner. The pre-assembled receiver 10/retainer 12 combination may be sterilized and individually packaged by the vendor, with each pre-assembly package having a discrete tracking number. Likewise, each shank 4 may be individually sterilized, packaged and given a tracking number that may be placed on the package. In other instances, an assembly 1 that includes the shank 4, receiver 10 and retainer 12 combination may be provided to the end user in a sterilized package with a tracking number.

Vendor pre-assembly of the receiver 10 with the open ring retainer 12 is shown in FIG. 13. The retainer 12 is bottom loaded into the receiver 10 through the receiver opening 81. In order to clear the receiver opening at the cylindrical surface 102, the retainer 12 is compressed with the opposed surfaces 127 and 128 that define the gap or slit 125 initially pressed toward one another an then maneuvered until a portion of the retainer base surface 112 overlaps onto the retainer top surface 110 with one of the end surfaces 127 or 128 located generally above the other end surface as shown in phantom in FIG. 13. Due to the small size of the retainer 12, such manipulation of the retainer 12 is possible and the resulting temporarily overlapping retainer is positioned within the receiver cavity 61. Once the retainer 12 is moved passed the cylindrical surface 102, the resilient retainer 12 is released and returns to a neutral or near neutral orientation as shown in solid lines in FIG. 13 with the small gap or slit 125 located between the opposed end surfaces 127 and 128. In both FIGS. 13 and 14, the now captured retainer 12 is blocked from exiting the bottom opening 81 of the receiver by the annular retainer seating surface 100. Now the retainer 12 is ready to be assembled with the shank 4 at the factory or, alternatively, be shipped to an end user as a sub-assembly (shown in FIG. 13); the end user (e.g., surgical staff) will thereafter assemble the combination with a desired shank 4.

Figure 14:
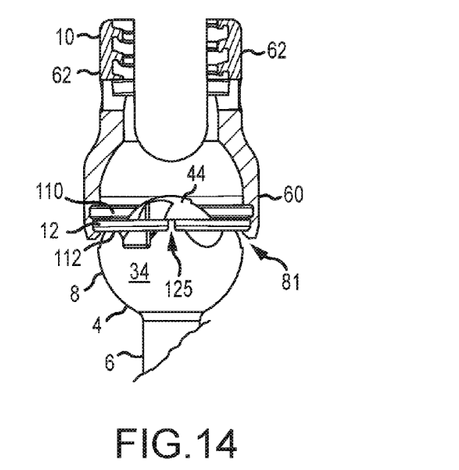
FIG. 14 is a front elevational view with portions broken away of the receiver and retainer of FIG. 13 and also showing the shank if FIG. 1 in an initial approach for assembly with the retainer, the shank being in partial front elevation.
Figures 15, 16:
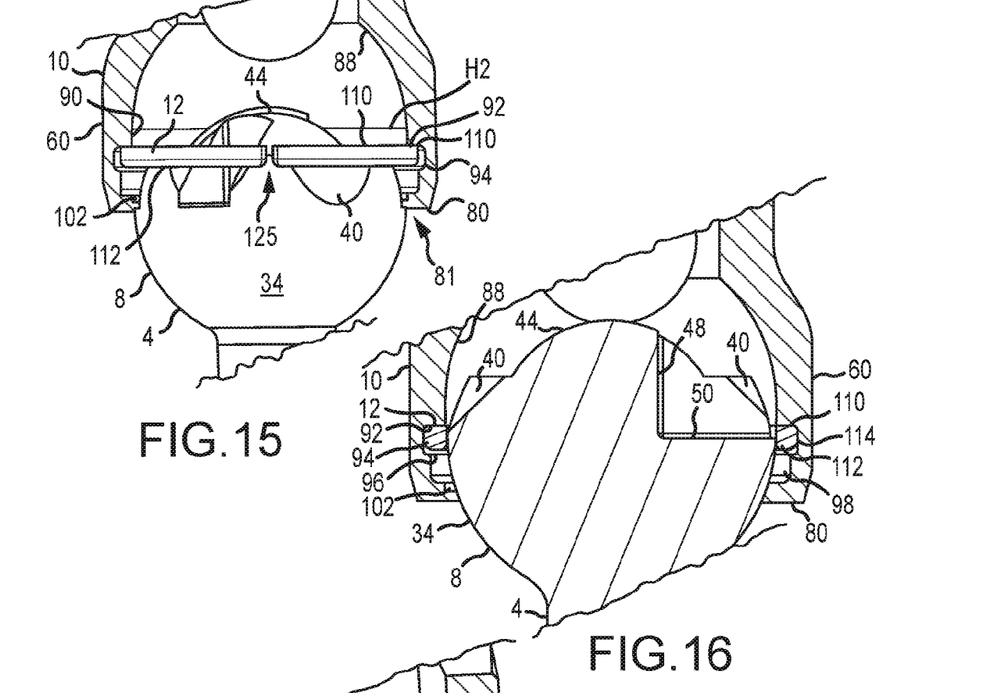
FIG. 15 is an enlarged and partial front elevational view with portions broken away of the receiver, retainer and shank of FIG. 14 and further showing the shank in an early stage of assembly with the retainer wherein the retainer is pushed upwardly against an inner surface of the receiver.
FIG. 16 is an enlarged and partial front elevational view with portions broken away, similar to FIG. 15, showing a head of the shank in a subsequent stage of assembly with the retainer, pressing the retainer outwardly to a configuration of maximum expansion against the receiver.
Figure 17:
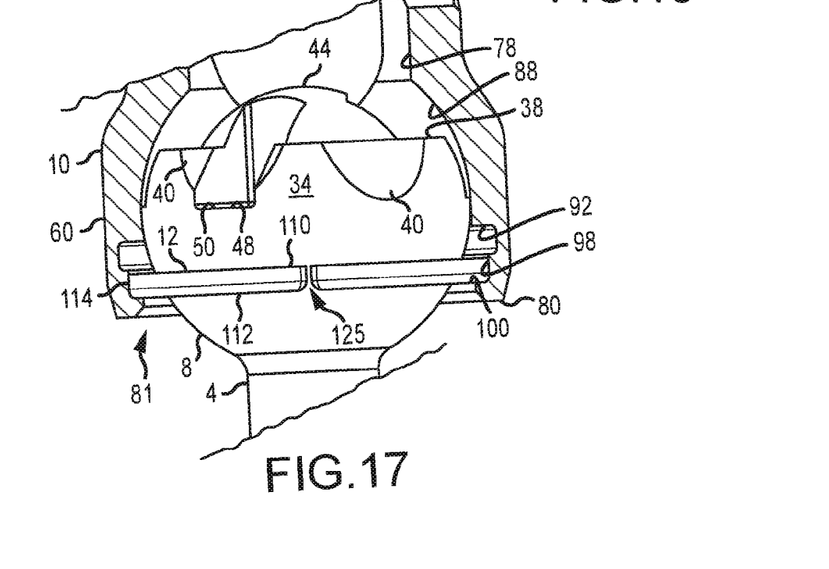
FIG. 17 is a partial front elevational view with portions broken away, similar to FIG. 16, showing the head of the shank pressed through the retainer and the retainer resiliently returned to a neutral or near neutral configuration.

With reference to FIGS. 14-18, the shank 4 is shown in various stages of assembly with the receiver 10 and captured retainer 12. If performed by the surgical staff, such stages may be performed either before or after the shank 4 is implanted into bone. FIGS. 14-18 illustrate a procedure in which the shank 4 is implanted into bone after the shank 4 is connected to the receiver and retainer sub-assembly. As shown in FIG. 14 the shank axis A and the receiver axis B are preferably aligned during assembly, however, exact axial alignment is not required. It is noted that although the retainer 12 is now captured within the receiver 10 such that very little tilt is allowed and thus most movement of the retainer 12 during assembly is axial or up and down movement along the receiver axis B, the retainer 12 may also be rotated with respect to the receiver 10 about the receiver axis B. With further reference to FIG. 14, the shank 4 is initially positioned beneath the receiver bottom surface 80 at the opening 81 and also beneath the retainer bottom surface 112 with the shank head 8 domed surface 44 initially moved up and through the retainer inner surfaces 122 and 118. With further reference to FIG. 15, as the shank head spherical surface 34 abuts against the retainer inner frusto-conical surface 122, the shank head 8 pushes the retainer 12 top surface 110 into abutment with the receiver ceiling surface 92. With reference to FIG. 16, as the shank head 8 continues to move upwardly toward the receiver arm u-shaped channel 62, the resilient ring retainer 12 cannot move upwardly and thus expands outwardly into the expansion chamber defined by the receiver surfaces 92, 94 and 96. Continued upward movement of the shank head surface 34 causes the surface 34 to slide first along the frusto-conical surface 122 and then the inner cylindrical surface 118 of the retainer 12, the gap 125 widening until the retainer outer cylindrical surface 114 abuts against the receive cylindrical surface 94 and the hemisphere H1 moves through and past the retainer ring 12. FIG. 16 shows the maximum expansion of the ring 12 and FIG. 17 shows a resilient return of the retainer 12 to a neutral or near neutral state after the shank hemisphere H1 passes through the retainer 12. FIG. 17 also shows how the retainer ring 12 then drops down to the retainer seat 100. In some embodiments, the shank 4 and the receiver 10 may need to be pulled in opposite directions away from one another to result in a fully seated retainer ring 12 as shown in FIG. 18. At this time, the shank head 8 is captured within the receiver 10, and as is shown in FIG. 18, the spherical surface 34 may be placed into engagement with the retainer 12 at the inner surface 120. The spherical surfaces 34 and 44 of the shank are not in engagement with any of the inner surfaces of the receiver 10. Only the retainer ring 12 is engagement with the receiver, but remains rotatable about the receiver axis B. At this time, the shank 4 is freely pivotable (side to side, forward to back and all pivoting movements therebetween) and rotatable with respect to the retainer 12 and thus also with respect to the receiver 10.

With reference to FIGS. 19-21, the fully assembled bone anchor assembly 1 made up of the connected shank 4, retainer 12 and receiver 10 are shown with the driver 24 for implanting the bone anchor shank 4 into the vertebra 17. As shown in FIG. 19, the driver 24 is received through the top opening 66 of the receiver and, as shown in FIGS. 20 and 21 is lowered until the three prongs 57 are fully seated in the shank three-slotted drive 42 with the driver prong base surfaces 58 abutting against the internal drive seating surfaces 50. The driver shaft 59 is then rotated until the bone screw shank 6 is implanted to a desired location in the vertebra 17. Then the driver 24 is removed out of the top opening 66 of the receiver 10.

In some procedures, the vertebra 17 may be pre-drilled to minimize stressing the bone and have a guide wire (not shown) inserted therein to provide a guide for the placement and angle of the shank 4 (in embodiments wherein the shank is cannulated) with respect to the vertebra. A further tap hole may be made using a tap with the guide wire as a guide. Then, the assembly 1 may be threaded onto the guide wire utilizing the cannulation bore. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires. As indicated earlier, if desired, the shank 4 alone may be driven into the vertebra 17 utilizing the pronged driver 24 without the remainder of the assembly 1, followed by pressing the receiver 10 and captured open retainer 12 onto the shank head 8. In such embodiments, the shank 4 may either be driven to a desired final location or may be driven to a location slightly above or proud to provide for ease in assembly with the pre-assembled receiver 10 and retainer 12. Thereafter, the shank 4 may be driven deeper into the vertebra 17 as illustrated in FIGS. 19-21 and previously described herein.

At this time and with reference to FIGS. 23-29, the receiver 10 may be articulated to a variety of angular positions with respect to the shank 4 prior to insertion of the rod 21 or closure top 18. Also with reference to FIGS. 22-29, the rod 21 is eventually positioned in an open or percutaneous manner in cooperation with the at least two bone screw assemblies 1. The closure structure 18 is then inserted into and advanced between the arms 62 of each of the receivers 10. The closure structure 18 is rotated, using a tool engaged with the inner drive 146 until a selected pressure is reached (typically about 40-50 inch pounds of torque) at which point the rod 21 frictionally engages and fixes against the domed surface 44 of shank head 8. The rod 21 pressing down on the surface 44 also urges the shank upper portion 8 spherical surface 34 toward the retainer inner surface 120 or outer edge thereof and into locking engagement therewith, the retainer 12 frictionally abutting and expanding outwardly against the receiver 10 at one or more of the surfaces 98, 99 and 100.

Figure 23:
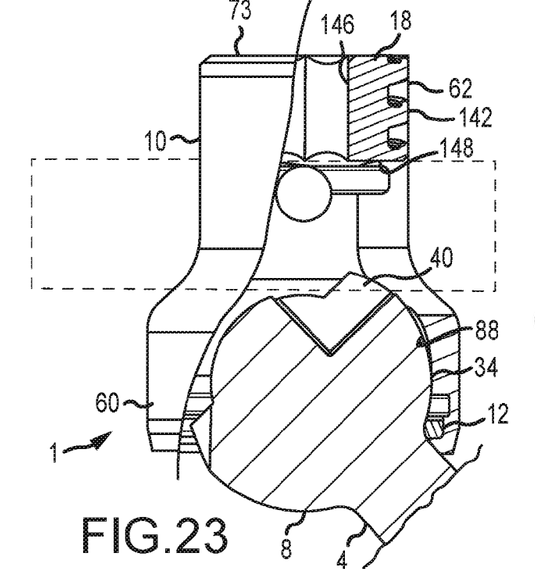
FIG. 23 is an enlarged and partial side elevational view with portions broken away of the assembly of FIG. 22, but with the shank pivoted to a forty-four degree angle with respect to the receiver in the sagittal plane with the shank directed caudally, the rod in phantom to show details of the assembly.
Figure 24:
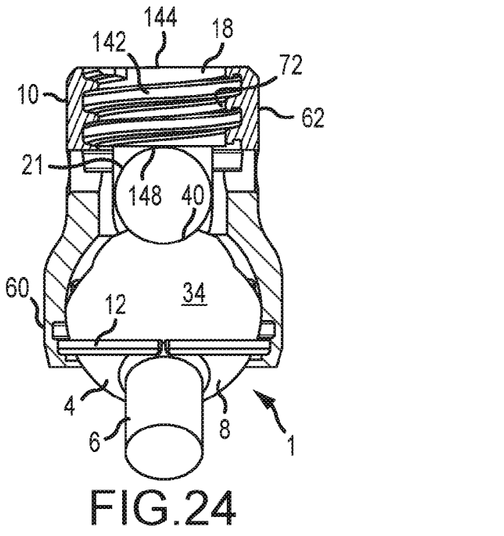
FIG. 24 is a reduced and partial rear elevational view of the assembly of FIG. 23 with portions of the receiver broken away to show details of the assembly.
Figure 27:
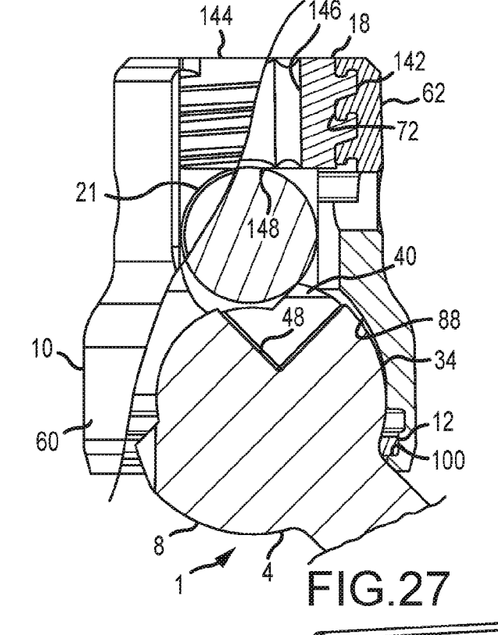
FIG. 27 is an enlarged and partial front elevational view with portions broken away of the assembly of FIG. 22 but with the shank pivoted to a forty-four degree angle with respect to the receiver in the transverse plane.
Figure 28:
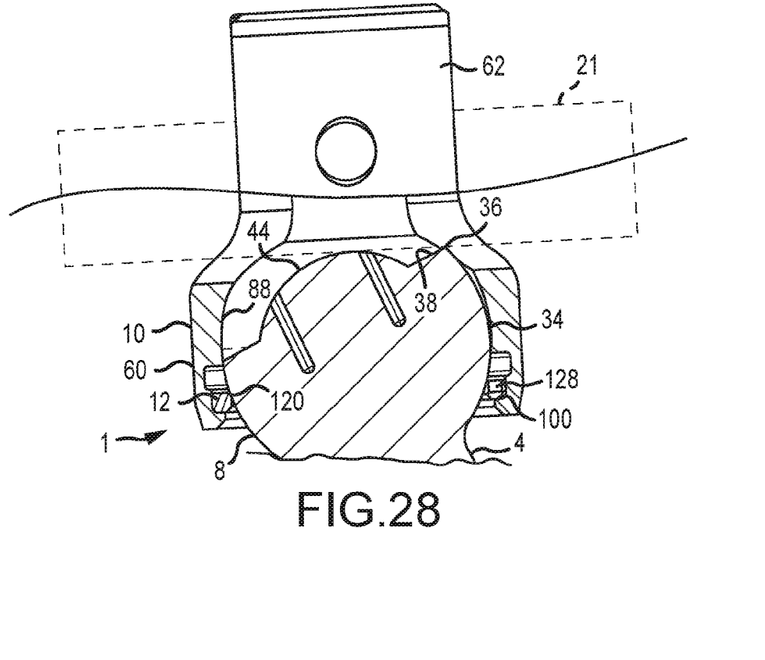
FIG. 28 is an enlarged and partial side elevational view with portions broken away of the assembly of FIG. 22 but with the shank rotated slightly and then pivoted to a twenty-four degree angle with respect to the receiver in the sagittal plane, the rod in phantom to show details of the assembly.
Figure 29:
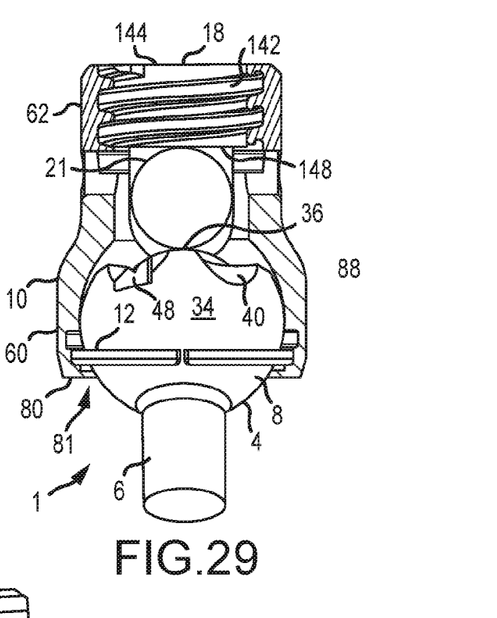
FIG. 29 is a reduced and partial rear elevational view of the assembly of FIG. 28 with portions of the receiver broken away to show the detail of the assembly.

FIG. 22 shows the assembly 1 in a locked position with the rod 21 and closure top 18 wherein the shank 4 axis A is substantially aligned with receiver axis B. FIGS. 23 and 24 show the assembly 1 in an alternative locked position with the rod 21 and the closure top 18 wherein the receiver 10 had been previously pivoted with respect to the shank 4 to a forty-four degree angle with the rod 21 being substantially received in one of the concave surface cut-outs 40 formed in the spherical surface 34 to allow for such extended pivot of the shank with respect to the receiver (shown in the sagittal plane and with the shank directed caudally). FIGS. 25 and 26 illustrate the same assembly 1 in an opposite forty-four degree angulation of the receiver with respect to the shank in a sagittal plane/cephalic direction. In such angulation, the rod 21 is also substantially received on one of the concave surface features 40 that includes a drive slot 48. However, as shown in FIG. 26, the rod 21 is adequately supported by remaining portions of the feature 40 and does not extend into the drive slot 48. Furthermore in both the cephalic and caudally directed extended angles, the spherical surface portions 34 located between the carved out features 40 are adequate to securely hold the shank head 8 in a fixed position against the retainer 12. With reference to FIG. 27, the receiver 10 has been pivoted with respect to the shank 4 (prior to locking of the closure 18 onto the rod 21) to a forty-four degree angle in the transverse plane. Finally, with reference to FIGS. 28 and 29, a twenty-four degree angulation between the shank 4 and the receiver 10 is shown along with rotation of the shank, showing how the rod may in some instances be fixed in position against the dome 44 and the edge 36 of the spherical surface 34.

It is to be understood that while certain forms of the present invention have been illustrated and described herein, it is not to be limited to the specific forms or arrangement of parts described and shown.

What is claimed and desired to be secured by Letters Patent is as follows:

1. A bone anchor assembly for securing an elongate rod to a bone, the elongate rod including a curved outer surface having a radius of curvature, the bone anchor assembly comprising:
   a receiver having a receiver axis of rotation, a pair of opposed upstanding arms extending upwardly from a base to define a U-shaped channel with inner surfaces configured to receive the elongate rod, and a cavity within the receiver base communicating with the U-shaped channel and with a bottom surface of the receiver through a lower opening in the receiver base; and
   a shank having a shank axis of rotation, a head, and an integral body extending distally from the head for fixation to the bone, the shank head being pivotably received within the receiver cavity with the shank body extending through the lower opening, the shank head including:
      a substantially-spherical lower surface extending upwardly and outwardly from the shank body to a circular perimeter edge of an annular surface located above an equator of the shank head, the lower surface having a first radius and being configured for frictional sliding and fixation within the receiver cavity, the perimeter edge being engageable with the elongate rod positioned within the U-shaped channel to define a first angle of articulation between the shank axis and the receiver axis;
      a substantially-spherical upper surface having a second radius that is less than the first radius extending upwardly and inwardly from the annular surface to form a dome top configured for direct engagement with the elongate rod; and
      at least one rounded cut-out formed transversely through the annular surface, the perimeter edge, and the lower surface to define a partially-cylindrical surface aligned with the dome top,
   wherein the at least one rounded cut-out is configured to receive the curved outer surface of the elongate rod when the elongate rod is received within the U-shaped channel to define a second angle of articulation that is greater than the first angle of articulation.

2. The bone anchor assembly of claim 1, wherein the at least one rounded cut-out further comprises a plurality of rounded cut-outs spaced symmetrically around the circumference of the shank head.

3. The bone anchor assembly of claim 1, wherein a radius of curvature of the at least one rounded cut-out is substantially equal to the radius of curvature of the elongate rod.

4. The bone anchor assembly of claim 1, further comprising a separate retainer located within the receiver cavity that retains the shank head within the receiver.

5. The bone anchor assembly of claim 4, wherein the retainer further comprises a resilient open ring that is bottom-loadable through the lower opening in the receiver base and expandable about the shank head in the receiver cavity during loading of the shank head into the receiver.

6. The bone anchor assembly of claim 5, wherein the receiver cavity is partially defined by a lower seat proximate the lower opening and an expansion chamber located above the lower seat, the lower seat being sized and shaped for engaging an outer surface of the retainer ring in a non-pivoting position while an inner surface of the retainer ring operatively engages the lower surface of the shank head to provide for the frictional sliding and fixation of the shank head within the receiver cavity.

7. The bone anchor assembly of claim 1, wherein the annular surface is perpendicular to the shank axis.

8. The bone anchor assembly of claim 1, wherein the substantially-spherical lower surface and the substantially-spherical upper surface are concentric.

9. The bone anchor assembly of claim 1, further comprising an internal drive structure formed into an upper hemispherical portion of the shank head.

10. The bone anchor assembly of claim 9, wherein the internal drive structure includes at least one drive slot extending downward from the upper surface, through the annular surface, and into a portion of the lower surface.

11. The bone anchor assembly of claim 10, wherein the at least one drive slot is formed into the at least one rounded cut-out.

12. The bone anchor assembly of claim 1, wherein the first angle of articulation is less than or about 24 degrees.

13. The bone anchor assembly of claim 1, wherein the second angle of articulation is less than or about 44 degrees.

14. The bone anchor assembly of claim 1, further comprising a discontinuous helically wound guide and advancement structure formed into the inner surfaces of the opposed upstanding arms.

15. The bone anchor assembly of claim 14, further comprising a closure structure having a continuous helically wound external thread directly engaging the discontinuous helically wound guide and advancement structure of the receiver to retain the elongate rod within the U-shaped channel and to urge the elongate rod against the dome top of the shank to maintain a current angle of articulation between the shank axis and the receiver axis.

* * * * *